United States Patent [19]
Wang et al.

[11] Patent Number: 5,928,148
[45] Date of Patent: Jul. 27, 1999

[54] METHOD FOR PERFORMING MAGNETIC RESONANCE ANGIOGRAPHY OVER A LARGE FIELD OF VIEW USING TABLE STEPPING

[75] Inventors: Yi Wang, New York; Howard M. Lee, Rye; Neil M. Khilnani, New York, all of N.Y.

[73] Assignee: Cornell Research Foundation, Inc., Ithaca, N.Y.

[21] Appl. No.: 08/924,105

[22] Filed: Sep. 5, 1997

Related U.S. Application Data

[60] Provisional application No. 60/048,286, Jun. 2, 1997.

[51] Int. Cl.$^6$ .................................................... A61B 5/055
[52] U.S. Cl. ............................ 600/420; 600/415; 324/306
[58] Field of Search ..................................... 600/410, 415, 600/416, 419, 420, 421, 422; 324/307, 309, 306

[56] References Cited

PUBLICATIONS

Time–Resolved Contrast–Enhanced 3D MR Angiography, MRM 36:345–351 (1996), Korosec, et al.
Gadolinium–enhanced MR AortographyRadiology 1994; 191:155–164, M.R. Prince, MD, PHD.
Dynamic MR Digital Subtraction Angiography Using Contrast Enhancement, Fast Data Acquisition, and Complex Subtraction, MRM 36:551–556 (1996), Wang, et al.
Abstract Presented Apr. 15, 1997 at 5th Annual meeting of ISMRM, K.Y. Ho, et al.

*Primary Examiner*—Marvin M. Lateef
*Assistant Examiner*—Shawna J Shaw
*Attorney, Agent, or Firm*—Quarles & Brady

[57] ABSTRACT

MRA data is acquired from a large region of interest by translating the patient to successive stations at which successive portions of the MRA data set are acquired. Patient movement is chosen to track a bolus of contrast agent as it passes through the region of interest to achieve maximum image contrast. In one embodiment a stationary local coil is supported adjacent the patient to acquire the MRA data and in another embodiment a multi-segment local coil moves with the patient and its segments are sequentially switched into operation.

11 Claims, 5 Drawing Sheets

METHOD FOR PERFORMING MAGNETIC RESONANCE ANGIOGRAPHY OVER A LARGE FIELD OF VIEW USING TABLE STEPPING

CROSS REFERENCE TO RELATED APPLICATION

This application is based on provisional application Ser. No. 60/048,286, filed on Jun. 2, 1997 and entitled "METHOD FOR PERFORMING MAGNETIC RESONANCE ANGIOGRAPHY OVER A LARGE FIELD OF VIEW USING TABLE STEPPING".

BACKGROUND OF THE INVENTION

The field of the invention is magnetic resonance angiography ("MRA"), and particularly, studies of the human vasculature using contrast agents which enhance the NMR signals.

Diagnostic studies of the human vasculature have many medical applications. X-ray imaging methods such as digital subtraction angiography ("DSA") have found wide use in the visualization of the cardiovascular system, including the heart and associated blood vessels. One of the advantages of these x-ray techniques is that image data can be acquired at a high rate (i.e. high temporal resolution) so that a sequence of images may be acquired during injection of the contrast agent. Such "dynamic studies" enable one to select the image in which the bolus of contrast agent is flowing through the vasculature of interest. Images showing the circulation of blood in the arteries and veins of the kidneys, the neck and head, the extremities and other organs have immense diagnostic utility. Unfortunately, however, these x-ray methods subject the patient to potentially harmful ionizing radiation and often require the use of an invasive catheter to inject a contrast agent into the vasculature to be imaged. There is also the issue of increased nephro-toxicity and allergic reactions to iodinated contrast agents used in conventional x-ray angiography.

Magnetic resonance angiography (MRA) uses the nuclear magnetic resonance (NMR) phenomenon to produce images of the human vasculature. When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins, and after the excitation signal $B_1$ is terminated, this signal may be received and processed to form an image.

When utilizing these signals to produce images, magnetic field gradients ($G_x$ $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

MR angiography (MRA) has been an active area of research. Two basic techniques have been proposed and evaluated. The first class, time-of-flight (TOF) techniques, consists of methods which use the motion of the blood relative to the surrounding tissue. The most common approach is to exploit the differences in magnetization saturation that exist between flowing blood and stationary tissue. Flowing blood, which is moving through the excited section, is continually refreshed by spins experiencing fewer excitation pulses and is, therefore, less saturated. The result is the desired image contrast between the high-signal moving blood and the low-signal stationary tissues.

MRA methods have also been developed that encode motion into the phase of the acquired signal as disclosed in U.S. Pat. No. Re. 32,701. These form the second class of MRA techniques and are known as phase contrast (PC) methods. Currently, most PC MRA techniques acquire two images, with each image having a different sensitivity to the same velocity component. Angiographic images are then obtained by forming either the phase difference or complex difference between the pair of velocity-encoded images.

To enhance the diagnostic capability of MRA a contrast agent such as gadolinium can be injected into the patient prior to the MRA scan. Excellent diagnostic images may be acquired using contrast-enhanced MRA if the data acquisition is properly timed with the bolus passage.

The non-invasiveness of MRA makes it a valuable screening tool for cardiovascular diseases. Screening typically requires imaging vessels in a large volume. This is particularly true for diseases in the runoff vessels of the lower extremity. The field of view (FOV) in MR imaging is limited by the volume of the $B_0$ field homogeneity and the receiver coil size (typically, the FOV<48 cm on current commercial MR scanners). The anatomic region of interest in the lower extremity, for example, is about 100 cm and this requires several FOVs, or stations, for a complete study. This requires that the patient be repositioned inside the bore of the magnet, the patient be relandmarked, scout images be acquired and a preparation scan be performed for each FOV. All of these additional steps take time and, therefore, are expensive. When contrast enhanced MRA is performed, the repositioning also necessitates additional contrast injections.

SUMMARY OF THE INVENTION

The present invention is a method for acquiring NMR data from a large region of interest by acquiring NMR data from a series of smaller fields of view which collectively span the large region of interest. The patient is automatically translated, or stepped, to a new position within the bore of the magnet by moving the patient table between the acquisition of each field of view. Scan parameters remain constant throughout the procedure and the separate reconstructed images are registered and combined to provide a single image of the large region of interest.

Another aspect of the present invention is to acquire the entire region of interest with one injection of contrast agent. The acquisition of each field of view is timed to correspond with the peak image contrast produced by the bolus of contrast agent. The order in which the separate fields of view are acquired and the speed of the patient translation between fields of view are selected to track the peak intraarterial contrast as the bolus transits through the region of interest.

Yet another aspect of the present invention is the use of local coils to improve the signal-to-noise ratio of the acquired MRA image. In one embodiment an array of local coils are positioned adjacent the patient and span the large region of interest. This local coil array moves with the patient as the table is translated from one station to the next, and successive segments of the array are connected to the receiver as they move into the imaging field of view. In a second embodiment a stationary local coil is supported adjacent the patient in the imaging field of view. The patient is translated through the imaging field of view and the stationary reception field of the local coil.

A general object of the invention is to efficiently acquire MRA data from a large region of interest. A single scan is performed in which MRA data is acquired from successive parts of the large region of interest. This is accomplished by translating the patient between acquisitions and concatenating the acquired data to form a single image of the entire region of interest.

Another object of the invention is to provide optimal contrast by timing the acquisition of MRA data with the arrival of contrast agent at each successive FOV in the region of interest. This is accomplished by acquiring data from which the velocity of the contrast agent bolus as it transits the region of interest is estimated. This velocity estimate is used to control the rate at which the patient is translated to successive FOVs during the scan and to track the peak in the contrast produced by the bolus.

Yet another object of the invention is to improve the SNR of the acquired image. This is accomplished by using a local coil which is positioned adjacent the patient. In one embodiment the local coil remains stationary as the patient is translated by it during the scan. In another embodiment a multi-segment local coil is carried by the patient. The local coil segments are successively switched into operation as the patient translates through the bore during the scan.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily-represent the full scope of the invention, however, and reference is made therefore to the claims herein for interpreting the scope of the invention.

DESCRIPTION OF THE PREFERRED EMBODIMENT

Figure 1:
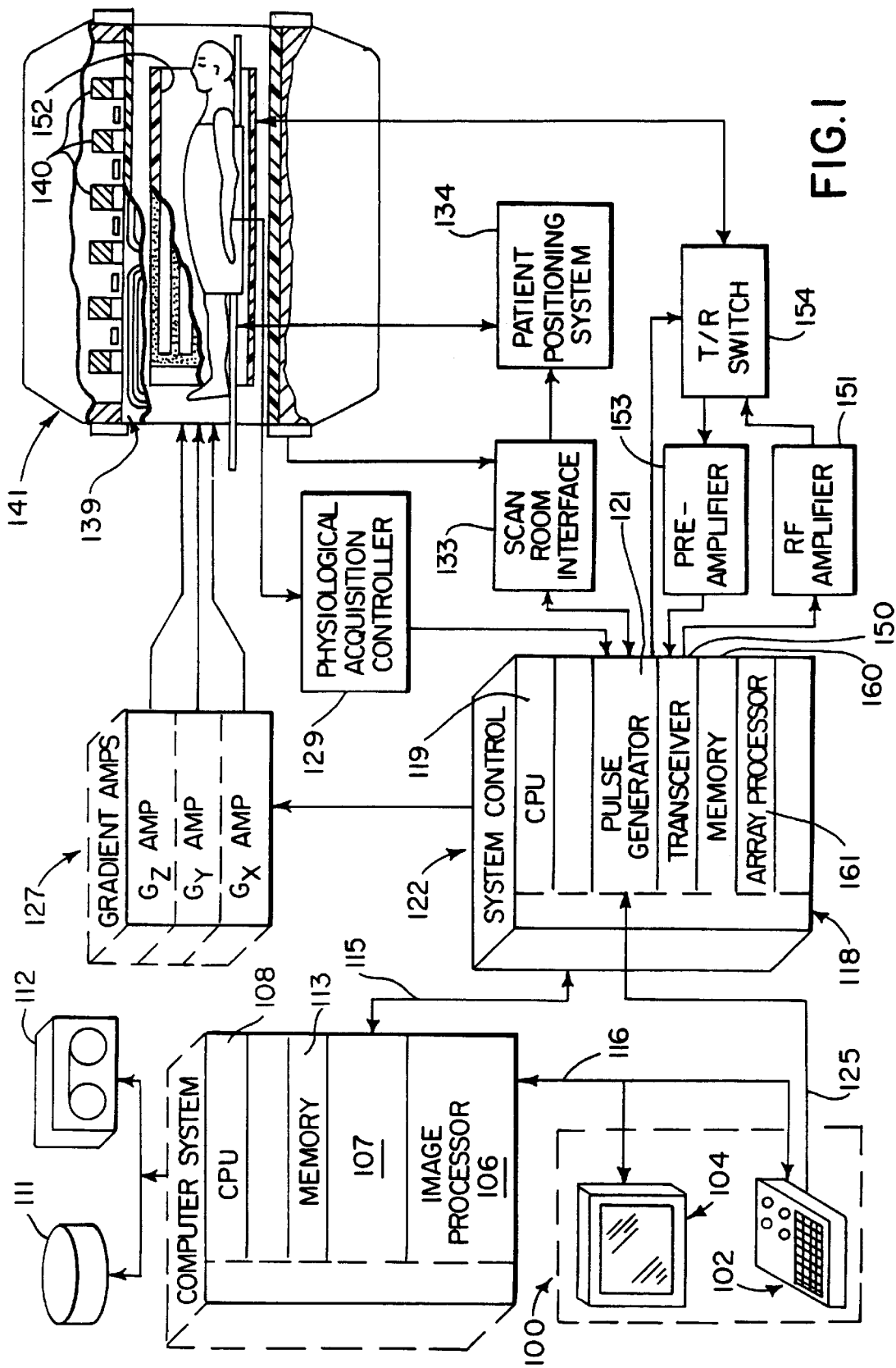
FIG. 1 is a block diagram of an MRI system which employs the present invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands from the pulse generator module 121 to move the patient to the sequence of desired positions to perform the scan in accordance with the present invention. The operator can thus control the operation of the patient positioning system 134 through the keyboard and control panel 102.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150.

Figure 7:
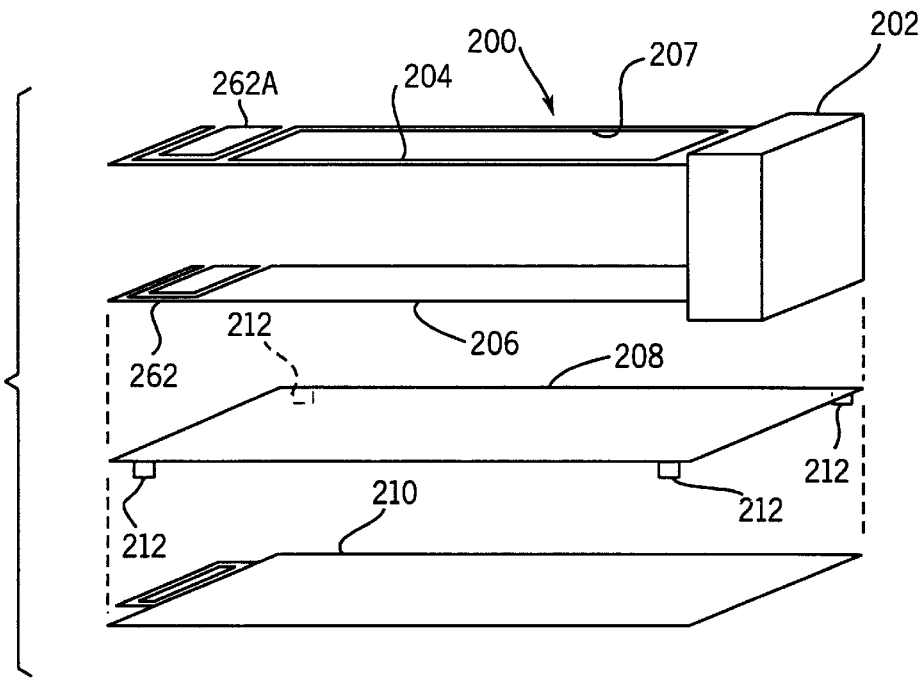
FIG. 7 is an exploded view of the supporting structure for a local RF coil used to practice the preferred embodiment.

The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF local coil to be used during the receive mode. In the preferred embodiment of the invention a single, stationary local coil described below and shown in FIG. 7 is switched into operation. In the alternative, a multi-segment local coil described below and shown in FIG. 8 may also be used. In this case, the separate segments of the local coil are switched into operation by the transmit/receive switch 154 as the patient is translated to successive stations during the scan.

The NMR signals picked up by the RF local coil are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

For a more detailed description of the transceiver 150, reference is made to U.S. Pat. Nos. 4,952,877 and 4,922,736 which are incorporated herein by reference.

Figure 2:
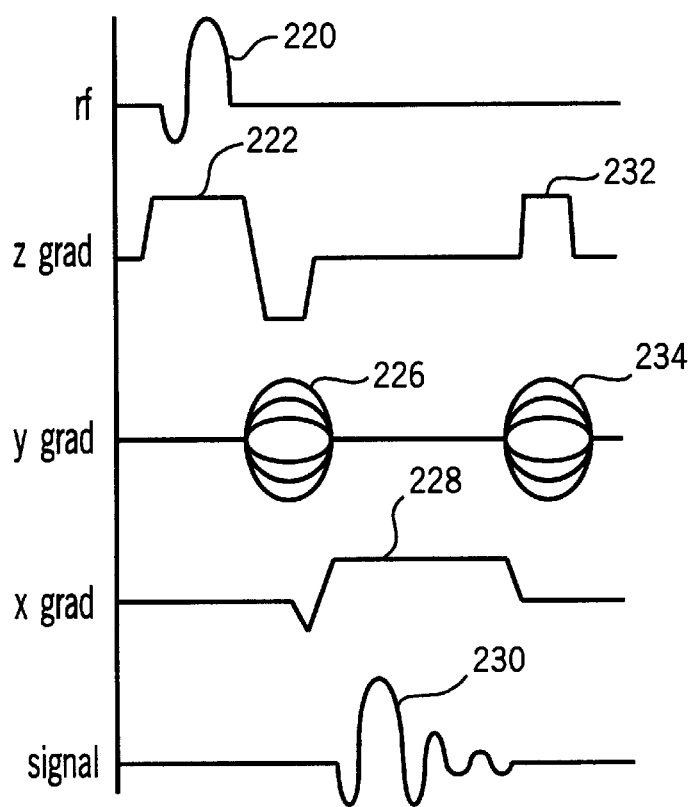
FIG. 2 is a graphic representation of a pulse sequence performed by the MRI system of FIG. 1 to practice a preferred embodiment of the invention.

While many pulse sequences may be used to practice the present invention, in the preferred embodiment a 2D gradient-recalled echo pulse sequence is used to acquire the NMR data. Referring particularly to FIG. 2, an RF excitation pulse 220 having a flip angle of 50° is produced in the presence of a slab select gradient pulse 222 to produce transverse magnetization in the 2D slab of interest (typically 100 to 150 mm thick). This is followed by a phase encoding gradient pulse 226 directed along the y axis. A readout gradient pulse 228 directed along the x axis follows and a partial echo (60%) NMR signal 230 is acquired and digitized as described above. After the acquisition, a spoiler gradient pulse 232 is applied along the z axis and a rewinder gradient pulse 234 is applied to rephase the magnetization before the pulse sequence is repeated as taught in U.S. Pat. No. 4,665,365.

As is well known in the art, the pulse sequence is repeated and the phase encoding pulse 226 is stepped through a series of values to sample the 2D k-space in the field of view. In the preferred embodiment 256 phase encodings are employed along the y axis. Sampling along the $k_x$ axis is performed by sampling the echo signal 230 in the presence of the readout gradient pulse 228 during each pulse sequence. It will be understood by those skilled in the art that only a partial sampling along the $k_x$ axis is performed and the missing data is computed using a homodyne reconstruction or by zero filling. This enables the echo time (TE) of the pulse sequence to be shortened to less than 1.8 to 2.0 ms and the pulse repetition rate (TR) to be shortened to less than 10.0 msecs.

Figure 3:
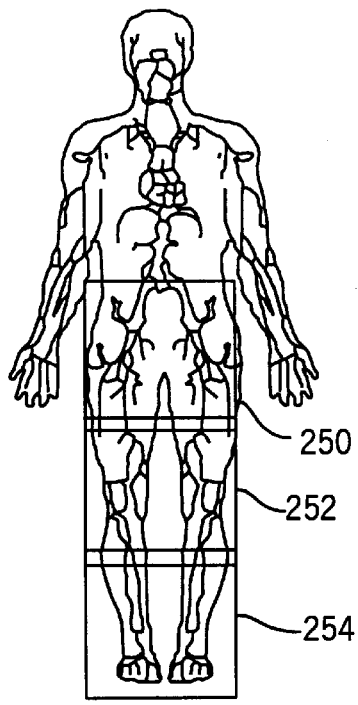
FIG. 3 is a pictorial representation of a patient illustrating a region of interest comprised of three overlapping fields of view.
Figure 4:
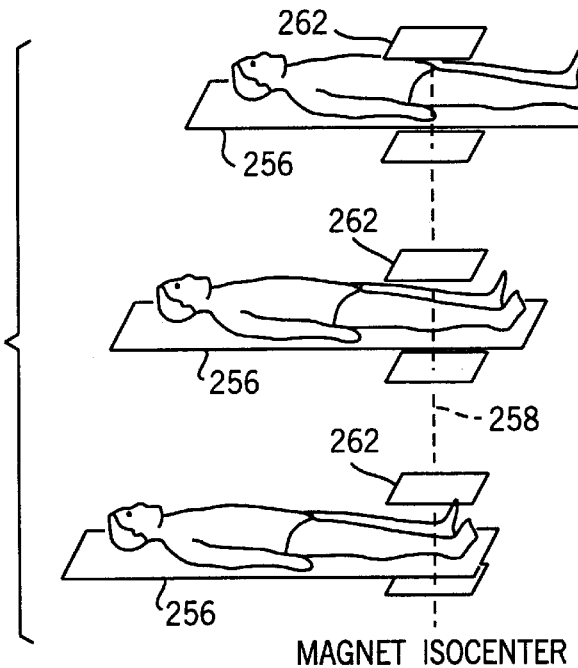
FIG. 4 is a pictorial representation of a patient within the bore of the MRI system of FIG. 1 to acquire the three fields of view shown in FIG. 3.

Referring to FIG. 3, an examination of the vasculature of a patient's legs can be performed by dividing up the region of interest into three overlapping fields of view indicated at 250, 252 and 254. As shown in FIG. 4, this is accomplished by moving a patient table 256 to three successive locations, or stations, within the bore of the magnet to align the respective centers of the field of view with the isocenter 258 of the MRI system. A local RF coil 262 such as a 4-coil array consisting of anterior and posterior subunits is positioned at the system isocenter and it remains stationary as the patient is translated by the table 256 to three different stations. At each station of the table 256 the pulse sequence of FIG. 2 is employed to acquire NMR data from which an image of the field of view may be reconstructed.

As shown in FIG. 7, a coil holder 200 has a closed end 202 which is attached to the carriage cover of the MRI system and supports an upper plate 204 and lower plate 206 which extend into the bore of the magnet, The end of the upper plate 204 supports the upper RF coil unit 262A which rests on the patient and slides smoothly over the patient during table translation. A rectangular opening 207 in the upper plate 204 provides space for the patient's feet. The lower plate 206 supports the lower RF coil unit 262B on its outer end which is positioned beneath the patient. The patient lies on an elevated table 208 and the lower plate 206 extends beneath the elevated table 208. The elevated table 208 rests on the sliding table 210 in the MRI system and is spaced therefrom by legs 212 to provide space for the lower plate 206. The patient may thus be translated between the RF coil units 262A and B which remain stationary at the system isocenter and in close proximity for optimal signal reception at all table stations.

Figure 9A:
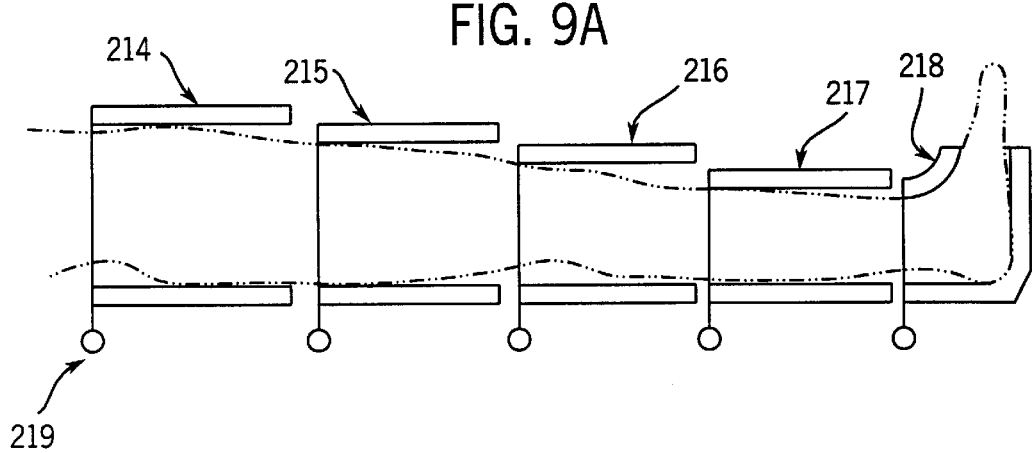
FIG. 9 is a schematic diagram of a multi-segment local coil used in an alternative embodiment of the invention.
Figure 9B:
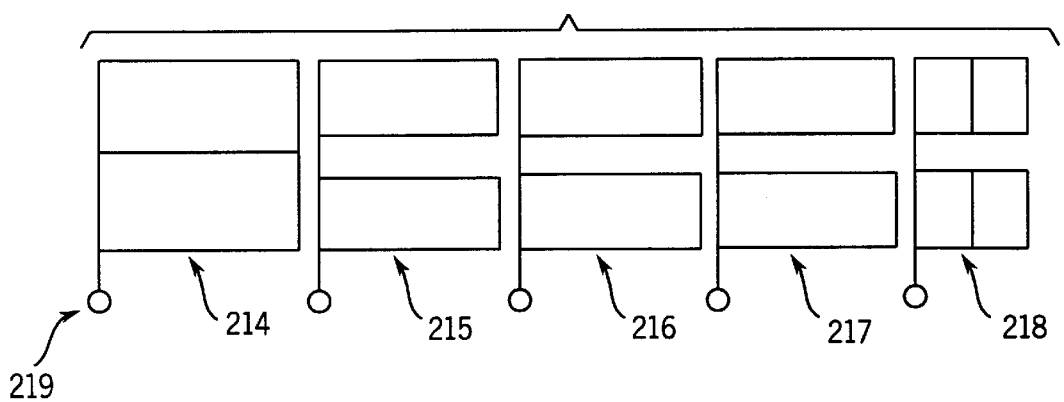

An alternative local coil structure which moves with the patient may also be used. Referring to FIGS. 9A and 9B, this alternative local coil is a coil array comprised of five coil segments 214–218, each comprised of four coil elements. The coil segments 214–218 are positioned on the patient and distributed along the entire region of interest to be imaged— in this case, the legs and feet. The coil elements are supported by fabric (not shown) which is sewn into a pant-like garment that clothes the patient's legs.

Each coil segment 214–218 has four coil elements that acquire NMR data from the FOV. Two of the coil elements are positioned on top, or anterior, of the lower extremity as seen in FIG. 9B, and the other two elements are positioned below, or posterior, of the lower extremity. The coil elements connect together to form one of the coil segments 214–218, and each is separately connected through terminals 219 to the above-described transmit/receive switch 154. Coupling between coil segments 214–218 is of little concern, because only one segment is operative at any moment during the scan. As the patient is translated to bring the successive coil segments 214–218 into the FOV of the MRI system, the aligned coil segment is connected to the system transceiver module 150. MRA data is acquired using that coil segment and the patient is then translated to the next station and the next coil segment is enabled.

The multi-element coil segments may be constructed using a number of well-known methods. Coupling between the separate coil elements is minimized to increase the SNR of the data acquired using the coil segment. Such decoupling is achieved using the methods taught in U.S. Pat. No. 4,825,162 issued to Roemer, et al., and entitled "*Nuclear Magnetic Resonance (NMR) Imaging With Multiple Surface Coils*" or U.S. Pat. No. 4,721,913 issued to Hyde, et al. and entitled "*NMR Local Coil Network*".

Figure 6:
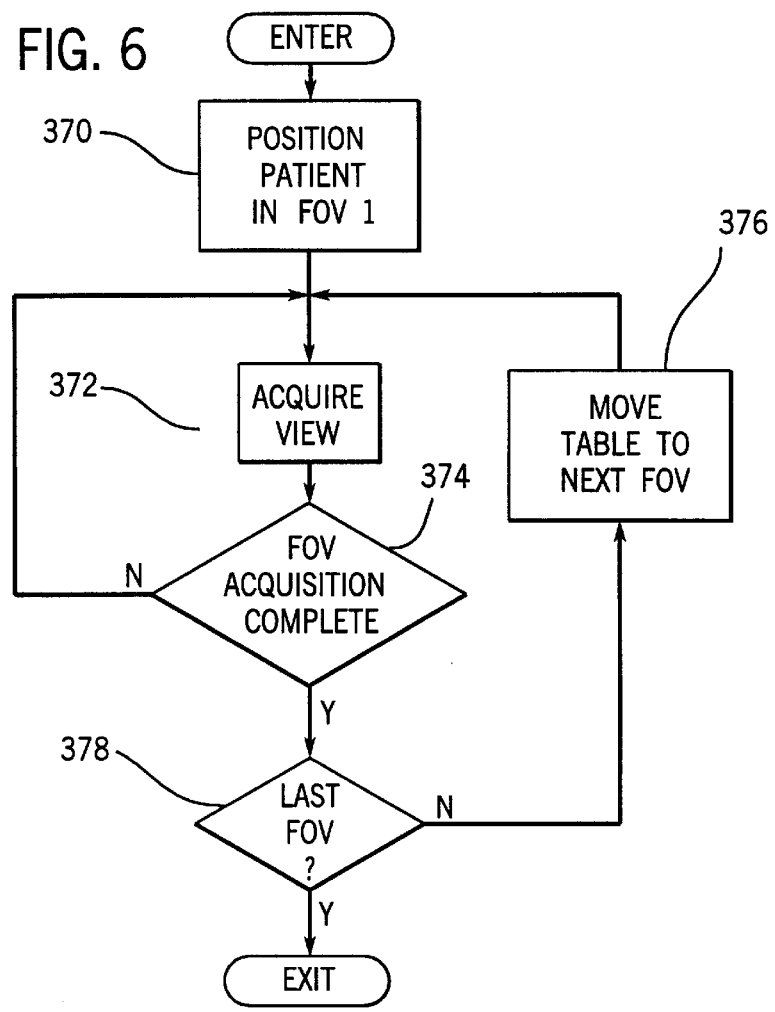
FIG. 6 is a flow chart of the sequence of steps performed by the MRI system of FIG. 1 to practice the preferred embodiment of the invention.

As shown in FIG. 6, the scan is performed under the direction of a stored program which directs the pulse generator module 121 to carry out a sequence of steps. As indicated by process block 370, the pulse control module 121 sends command signals to the patient positioning system 134 which moves the table to align the first FOV at the system isocenter 258. A loop is then entered in which NMR data is acquired for a complete image. More specifically, the pulse control module 121 directs the MRI system to perform the pulse sequence of FIG. 2 to acquire one view of NMR data as indicated at process block 372. Phase encodings are stepped as described above and additional views are acquired until all of k-space has been sampled and the acquisition is complete as determined at decision block 374.

At the completion of the first image acquisition the pulse control module 121 commands the patient positioning system 134 to move the table 256 to the next station to align the next field of view at the system isocenter 258 as indicated at process block 376. In the preferred embodiment this distance is 25 cm. Another image is then acquired at 372 and 374. This sequence of acquiring an image and moving the patient table 256 continues until the last field of view in the scan has been acquired as determined at decision block 378. Both the FOV sizes and the separation between the anterior and posterior coils may vary from FOV to FOV for optimal image resolution and signal-to-noise ratio.

The acquired field of view images are registered with each other and combined to form a single image of the much larger region of interest. The patient is immobilized to the table 256 with straps (not shown) to minimize misregistration between the field of view images. In addition, a marker made of a contrast agent solution which produces a high level signal can be placed along side the patient and used to align each field of view image such that they are in registration with each other and form a single, contiguous image of the entire region of interest.

Figure 5:
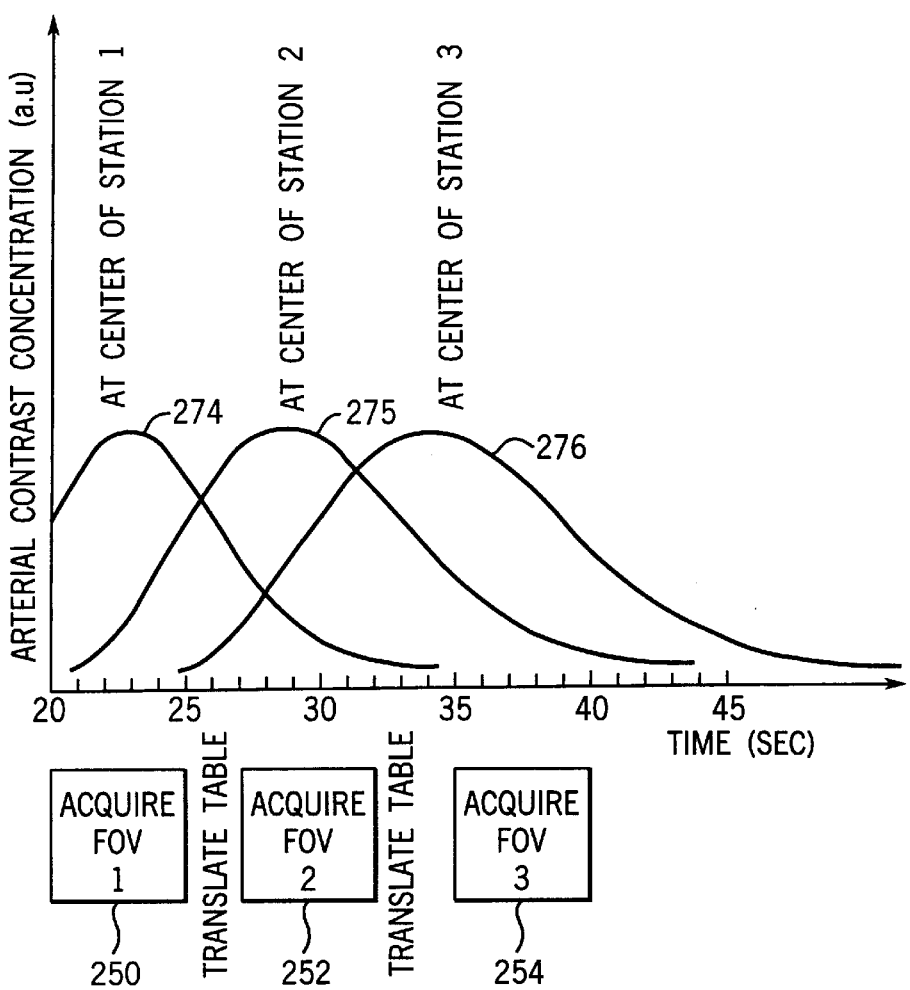
FIG. 5 is a graphic representation of the contrast bolus curve.

In the preferred method the acquisition of each FOV is timed to occur when maximum image contrast is produced by a contrast agent administered intravenously to the patient. A test bolus (eg. 5 ml of gadolinium) is administered intravenously to measure the bolus timing curve at a predetermined region of interest, typically the second FOV. As shown in FIG. 5, for example, the curve 274 peaks in the first FOV 250 at approximately 23 seconds after the contrast agent is administered, the curve 275 peaks in the second FOV 252 at approximately 29 seconds after the contrast agent is administered and the curve 276 peaks in the third FOV 254 at approximately 35 seconds after contrast administration. This establishes when the data should be acquired for best image contrast.

If the three FOVs 250, 252, 254 are acquired in order, the intraarterial column of contrast agent is imaged as it transits through the patient's legs. To maximize image contrast, the velocity of the bolus movement is estimated and the table translation is timed to acquire each FOV at peak contrast. One way to estimate the bolus velocity is to measure the arterial velocity (averaged over the cardiac cycle) by acquiring a phase contrast image through the artery of interest in the center of the region of interest as described in U.S. Pat. No. Re 32,701. Blood flow velocity can be determined from this image and an estimate made of the bolus velocity. Another way to estimate the bolus velocity is to perform a timing scan in which the bolus advancement through the FOV is monitored using a high temporal frame rate. This second method provides a rapid estimation of bolus velocity that is accurate enough to use with the present invention. From this velocity estimate and the peak contrast timing for the central FOV 252, the timing for the acquisition of the FOVs 250 and 254 can be calculated. These timings will determine the rate of table translation between FOV acquisitions.

The timing for table translation is estimated from three parameters: the estimate of bolus velocity; the duration of data acquisition at each FOV; and the time for moving the patient from one FOV to the next. Optimal results are achieved in the preferred embodiment if the leading edge of the bolus contrast agent has flowed into the next FOV for about 5 sec ($T_{12}$). The time for each additional FOV ($T_s$) is the time for table translation from one FOV to the next (3 seconds or less if performed manually), and the imaging duration (about 5–7 sec). The total length of the contrast agent bolus column ($L_b$) required to perform the scan can then be estimated from the following equation:

$$L_b = FOV + T_{12} \cdot V_b + (N_s - 1)(T_s \cdot V_b - L_s).$$

Here $N_s$ is the number of FOVs to be imaged, and $V_b$ is the estimated bolus velocity. $L_s$ is the table translation distance between stations, which is slightly smaller than FOV to provide overlapping acquisitions between adjacent stations. A constant bolus velocity is used in the above equation. This concept can also be extended straight forwardly to the case of varying bolus velocity using integration. The imaging duration at each station is kept at several seconds to account for velocity variation as the contrast column travels to the more peripheral FOVs. Accordingly, the contrast duration is $T_b = L_b/V_b$ and the injection duration is less than this by the cardiac dispersion effects ($\tau_c \sim 5$ seconds). For a given injection rate, ($R_i$) the required contrast dose is as follows:

$$D = (L_b/V_b - \tau_c) \cdot R_i.$$

Figure 8:
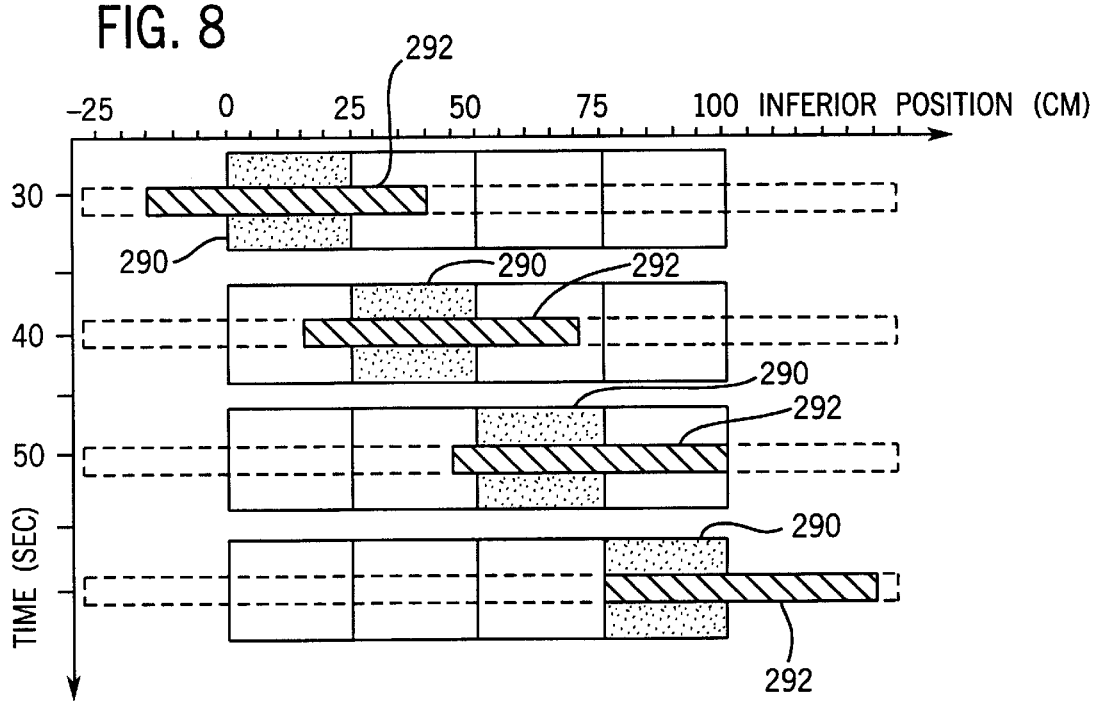
FIG. 8 is a graphic illustration of how the contrast agent bolus is tracked.

An example of using this timing and contrast dose information is illustrated in FIG. 8. In this example, the length of each imaging region is 25 cm and indicated by shaded region 290, and it is translated to the second, third and fourth FOVs at 30, 40 and 50 seconds respectively. The contrast agent bolus 292 transits the region at a speed of 3 cm/sec and imaging of the first FOV continues until the leading edge of the contrast agent bolus 292 is 5 seconds into the second FOV. The time at each additional FOV is 10 seconds, 7 seconds for acquiring image data and 3 seconds for moving the next FOV into the imaging region 290. The total length of the contrast agent bolus is 55 cm, which corresponds to a bolus duration of 18.3 seconds. A bolus injection duration of 15 seconds is used, and at an injection rate of 1 cc/sec., the total dose is 15 cc (using 3.3 sec $\tau_c$).

As is well known in the art, "mask" images may also be acquired before contrast agent is administered. In the preferred embodiment, the mask images are acquired before bolus injection at each of the stations. The above described contrast enhanced acquisition is then performed and a complex subtraction of corresponding voxels in the mask image from the reconstructed image is performed to further enhance image quality.

The preferred method for practicing the invention includes conducting a "scout scan" to confirm that the vasculature of interest is within the FOV of at least one of the stations. This is followed by a "timing scan" in which information is acquired regarding the arrival and velocity of the contrast agent bolus, and by a "mask scan" in which the mask image data is acquired. And finally, the "bolus tracking MRA scan" is conducted as described above and shown in FIG. 6. The following is an exemplary procedure for carrying out these steps in a four station scan of a patient's legs.

Scout Scan

A multiple location, sagittal acquisition using a 2D fast gradient echo sequence (FOV=40 cm, TE/TR=2/9, receiver bandwidth=16 kHz, 256×256, ½ FOV, total acquisition time ~15 sec) is performed at the first station. The patient is translated to the second station and the same scan is repeated immediately without any prescan. This process repeats until all stations are imaged. For a 4-station scout scan, the total imaging time is about 70 sec (allowing 10 seconds for each table motion).

Timing Scan

A thick coronal slab timing acquisition is typically performed at the second station using a gadolinium contrast agent test dose (3–5 mL, at 1 mL/sec injection rate) and a 2D fast gradient echo sequence (FOV=32–40 cm, 130–170 mm thick, TE/TR=2/9, receiver bandwidth=16 kHz, 256× 160–192, 40–60 image frames, total acquisition time ~60–90 sec to ensure the capture of the contrast peak). From this timing acquisition, the arrival time of the contrast agent in the FOV is measured, and the bolus velocity is estimated based on the time required for the bolus to transit the FOV.

Mask Scan

Similar to the timing scan, a thick coronal slab containing all arteries of interest is acquired using a fast 2D gradient echo sequence (FOV=32 cm, 130–170 mm thick, TE/TR= 2/9, receiver bandwidth=16 kHz, 256×160–192, 40–60 image frames, total acquisition time ~60–90 sec. In contrast to the timing scan, the table is translated to each station at times determined by the timing scan and mask data is acquired at each FOV.

Bolus Tracking MRA Scan

The contrast agent is administered and a scan is conducted using the same prescription as the mask scan. As with the mask scan, the data acquisition is begun at the time, and the table is translated at the times determined by the timing scan.

Studies were performed on volunteers using the preferred embodiment of the invention. First, a single station timing acquisition was performed at the second station with 0.05 mmol/kg intravenous gadolinium injection at a rate of 1.5–2 mL/sec followed with a 20 mL saline flush. The contrast concentration time course was measured at the proximal, middle and distal locations. The time to peak (or the onset of a plateau) was estimated.

Next, a multiple station acquisition without contrast injection was performed to obtain mask data. Immediately following the mask acquisition, a gadolinium-enhanced bolus tracking acquisition was performed with a gadolinium dose of 0.1–0.2 mmol/kg. The table translation from the first station to the second station occurred at the peak time of the contrast curve at the distal location of the second station. Table translations were 20–30 cm per step, providing 2–12 cm overlap. Hand injection and later an MR compatible power injector (Spectris MR Injector, MedRad, Pittsburgh, Pa.) was used. All infusions were followed immediately by a 30 mL saline flush.

In one patient, for example, the timing bolus arrived at the popliteal artery approximately 27 sec after injection, and it took approximately 6 sec to traverse the central station. Three-station acquisitions were planned for this subject. A 15 mL dose at 1 mL/sec injection rate was used for bolus tracking acquisition (15 sec injection time). Accordingly, table translation from the first station to the second station occurred between 34–36 sec after injection, allowing about 10 sec for imaging the first station. Imaging time at the second station was 12 sec. Then the table was translated to the third station between 48–50 sec after injection. The total acquisition time was 60 sec. All arteries from the external iliac artery in the pelvis through the anterior tibial and posterior tibial arteries at the ankle are well depicted.

Our results support the hypothesis that MRA of the lower extremity can be performed rapidly using a bolus tracking strategy, a stepping table, and a 2D MR imaging technique. With this bolus tracking MR technique, MR angiography of the entire lower extremity can be performed in approximately one minute. Including time for acquiring the scout, bolus timing and mask data sets, the total examination time for MRA of the entire lower extremity is between ten and fifteen minutes. This is a substantial reduction in scan time from that of the standard TOF technique (typically 60–90 minutes).

The 2D acquisition employed in this study provides high temporal resolution while complex subtraction of the mask image provides high contrast-to-noise ratio with minimal artifacts. A frame rate of 1–2 sec per image can be maintained while providing 1 mm×1 mm in-plane resolution with good SNR. This rapid acquisition enables imaging of the same contrast bolus sequentially as it transits the arterial tree. Imaging of each station for five to ten seconds permits the acquisition of the contrast enhanced lower extremity arteries in 30 seconds. This is less than the time required for imaging one station using a 3D acquisition. Consequently, a much smaller contrast dose can be used in bolus tracking 2D MR. An alternative way to take advantage of 2D acquisition is to acquire multiple projections at each station by alternating slab orientation. Because the in-plane resolution is higher than that of a MIP image from a 3D acquisition, this may be a more effective way to obtain additional spatial information of the targeted arteries.

An alternative method to the "bolus tracking" of the preferred embodiment is to separately administer contrast agent prior to each FOV acquisition. In this case a mask image is acquired just prior to each bolus injection, the bolus is administered, and the image acquisition for the particular FOV is performed when peak contrast is obtained in that FOV. The table is then translated to the next FOV and the process is repeated.

Other data processing techniques may be used to generate angiograms. Methods other than complex subtraction, such as digital filters, may be used to generate angiograms. The criteria for digital filter design is to extract dynamic contrast (or signal variation) from a temporal series of images, and vessel contrast is determined by this dynamic contrast. For example, matched filters can be used to generate an angiogram that is a sum of individual arteriograms generated by complex subtraction.

Another application for the invention is to image the aorta in the body trunk. The aortic arch and the abdominal aorta can be image in two separate FOVs using a fast 3D acquisition technique (temporal resolution<one 3D volume per 20 sec) and contrast infusion. In addition, the table stepping between different FOVs can be an important technical component for general fluoroscopic MR imaging and MRI-guided interventions.

We claim:

1. A method for producing an image with an MRI system, the steps comprising:

a) positioning a patient in the MRI system;

b) acquiring NMR image data from the patient over a first field of view while the patient is stationary relative to the MRI system;

c) translating the patient in the MRI system;

d) acquiring NMR image data from the patient over a second field of view while the patient is stationary relative to the MRI system;

e) registering the NMR image data acquired over the first and second field of views and reconstructing an image over a region of interest which includes the first and second field of views.

2. The method as recited in claim 1 in which a contrast agent is administered to the patient and the acquisition of NMR image data over the first and second field of views occurs when the contrast agent provides substantially maximum contrast therein.

3. The method as recited in claim 2 which includes acquiring NMR data that indicates the velocity of the contrast agent through the region of interest.

4. The method as recited in claim 3 in which the translation of the patient in the MRI system is controlled in part by the indicated contrast agent velocity.

5. The method as recited in claim 1 in which the patient is translated additional times, NMR image data is acquired from additional field of views, and the reconstructed image includes NMR image data from the additional field of views.

6. The method as recited in claim 1 in which the patient is translated a preselected distance and the NMR image data acquired over the first field of view is registered with the NMR image data acquired over the second field of view by establishing their relative positions using said preselected distance.

7. The method as recited in claim 1 in which the NMR image data is acquired using a local RF coil which is positioned adjacent the patient and which remains stationary as the patient is translated.

8. The method as recited in claim 1 in which the NMR image data is acquired using a local RF coil having a plurality of coil segments which are supported by the patient, and as the patient is translated different coil segments are switched into operation to acquire NMR image data.

9. The method as recited in claim 1 in which a contrast agent is administered to the patient and a timing scan is conducted to estimate the optimal time at which step b) is to be performed, and to estimate the velocity of the contrast agent as it flows through one of said field of view.

10. The method as recited in claim 9 in which the performance of step c) is determined in part by the estimated velocity of the contrast agent.

11. A method for producing an image with an MRI system, the steps comprising:

a) performing a timing scan in which a contrast agent is administered to a patient and the arrival time and the velocity of the contrast agent in a region of interest is estimated from NMR data acquired by the MRI system;

b) performing a bolus tracking scan to acquire NMR data from the region of interest by translating the patient to a plurality of stations and acquiring NMR image data from a corresponding plurality of field of views within the region of interest; and c) reconstructing the image from NMR data acquired from all of said field of views;

wherein the start of the bolus tracking scan is determined by said estimated arrival time and the translation of the patient to said plurality of stations is timed in part by said estimated velocity.

* * * * *